United States Patent [19]

Iqbal et al.

[11] Patent Number: 4,720,305
[45] Date of Patent: * Jan. 19, 1988

[54] MIXTURES OF PIGMENTS

[75] Inventors: Abul Iqbal, Ettingen; Johannes Pfenninger, Marly; Alain C. Rochat, Fribourg; Fridolin Bäbler, Marly, all of Switzerland

[73] Assignee: Ciba-Geigy Corporation, Ardsley, N.Y.

[*] Notice: The portion of the term of this patent subsequent to Apr. 1, 2003 has been disclaimed.

[21] Appl. No.: 794,933

[22] Filed: Nov. 4, 1985

[30] Foreign Application Priority Data

Nov. 7, 1984 [CH] Switzerland ................. 5335/84

[51] Int. Cl.$^4$ ............................................. C08K 5/16
[52] U.S. Cl. ................. 106/288 Q; 106/22; 106/23
[58] Field of Search ........... 106/288 Q, 309, 22, 106/23

[56] References Cited

U.S. PATENT DOCUMENTS

| | | | |
|---|---|---|---|
| 4,271,301 | 6/1981 | Lotsch et al. | 106/288 Q |
| 4,415,685 | 11/1983 | Iqbal et al. | 106/253 |
| 4,579,949 | 4/1986 | Rochat et al. | 524/104 |
| 4,585,878 | 4/1986 | Jost et al. | 548/453 |

Primary Examiner—Paul Lieberman
Assistant Examiner—W. Thompson
Attorney, Agent, or Firm—Luther A. R. Hall

[57] ABSTRACT

The invention relates to a mixture of at least two different pigments of the formula

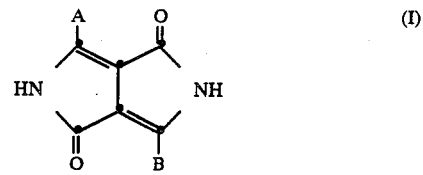

with the difference lying in the meanings of the radicals A and B, in which the formula (I) A and B are the same or different alkyl, aralkyl, cycloalkyl, carbocyclic or heterocyclic aromatic radicals, which mixture of pigments is obtainable by (a) reacting 1 mole of a disuccinate with 1.75 to 1.998 moles of a nitrile of the formula ACN and 0.002 to 0.25 mole of a nitrile of the formula BCN or of a mixture of several nitriles of the formula BCN, the radicals B of which are different from A, or (b) reacting 1 mole of a lactam of formula (II) or of an enamine of formula (III)

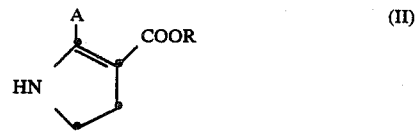

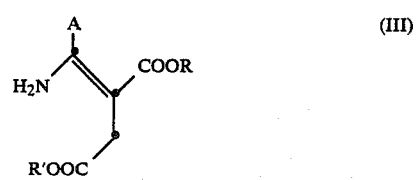

in which formula each of R and R' independently of the other is alkyl or aryl, with 0.75 to 0.998 mole of a nitrile of the formula ACN and 0.25 to 0.002 mole of a nitrile of the formula BCN or of a mixture of several nitriles of the formula BCN, the radicals B of which are different from A, in an organic solvent, in the presence of a strong base and at elevated temperature, and subsequently hydrolyzing the resultant reaction product.

The mixture of pigments is suitable for coloring material of high molecular weight, in particular plastics and lacquers, in red shades of excellent fastness properties.

15 Claims, No Drawings

MIXTURES OF PIGMENTS

The invention relates to mixtures of different 1,4-diketopyrrolo[3,4-c]pyrrole pigments. Pigments of this kind are known from U.S. Pat. No. 4,415,685. In various respects, particularly with regard to their colour strength, these pigments are not always satisfactory. It has now been found that mixtures of such compounds have surprisingly better pigment properties.

Accordingly, the invention relates to a mixture of at least two different pigments of formula (I)

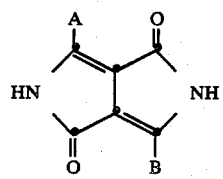
(I)

with the difference lying in the meanings of the radicals A and B, in which formula (I) A and B are the same or different alkyl, aralkyl, cycloalkyl, carbocyclic or heterocyclic aromatic radicals, which mixture of pigments is obtainable by (a) reacting 1 mole of a disuccinate with 1.75 to 1.998 moles of a nitrile of the formula ACN and 0.002 to 0.25 mole of a nitrile of the formula BCN or of a mixture of several nitriles of the formula BCN, the radicals B of which are different from A, or (b) reacting 1 mole of a lactam of formula (II) or of an enamine of formula (III)

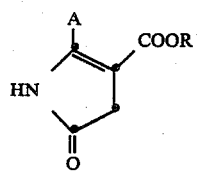
(II)

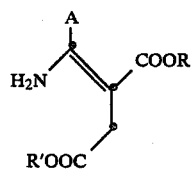
(III)

in which formulae each of R and R' independently of the other is alkyl or aryl, with 0.75 to 0.998 mole of a nitrile of the formula ACN and 0.25 to 0.002 mole of a nitrile of the formula BCN or of a mixture of several nitriles of the formula BCN, the radicals B of which are different from A, in an organic solvent, in the presence of a strong base and at elevated temperature, and subsequently hydrolysing the resultant reaction product.

A and B in formulae (I), (II) and (III) as alkyl groups may be branched, unbranched or cyclic, saturated or unsaturated, and contain preferably 1 to 18, in particular 1 to 12 and most preferably 1 to 6, carbon atoms, e.g. methyl, ethyl, isopropyl, sec-butyl, tert-butyl, tert-amyl, cyclohexyl, octyl, decyl, dodecyl or stearyl.

A and B as aralkyl groups are preferably those which contain a preferably mono- to tricyclic, most preferably mono- or bicyclic, aryl radical which is attached to a branched or unbranched alkyl or alkenyl group containing 1 to 12, preferably 1 to 6 and most preferably 1 to 4, carbon atoms. Examples of such aralkyl groups are benzyl and phenylethyl.

A and B in formulae (I), (II) and (III) as isocyclic aromatic radicals are preferably mono- to tetracyclic, most preferably mono- or bicyclic, radicals, e.g. phenyl, diphenylyl or naphthyl.

A and B as heterocyclic aromatic radicals are preferably mono- to tricyclic radicals. Said radicals may be purely heterocyclic or may be a heterocyclic ring which contains one or more fused benzene rings, e.g. pyridyl, pyrimidyl, pyrazinyl, triazinyl, furanyl, pyrrolyl, thiophenyl, quinolyl, coumarinyl, benzofuranyl, benzimidazolyl or benzoxazolyl. Both the isocyclic and the heterocyclic aromatic radicals may contain the conventional non-watersolubilising substituents as cited for example in U.S. Pat. No. 4,579,949.

The preferred starting materials employed in the preparation of the mixtures of pigments of the present invention are nitriles of formula (IV)

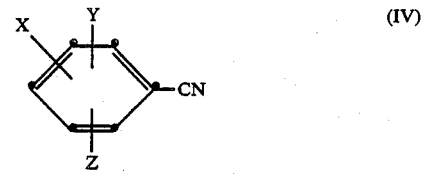
(IV)

wherein each of X, Y and Z independently is hydrogen, halogen, carbamoyl, cyano, trifluoromethyl, $C_2$–$C_{13}$alkylcarbamoyl, $C_1$–$C_{12}$alkyl, $C_1$–$C_{12}$alkoxy, $C_1$–$C_{12}$alkylmercapto, $C_2$–$C_{13}$alkoxycarbonyl, $C_2$–$C_{13}$alkanoylamino, $C_1$–$C_{12}$monoalkylamino, $C_2$–$C_{24}$dialkylamino, or is phenoxy, phenylmercapto, phenoxycarbonyl, phenylcarbamoyl or benzoylamino, each unsubstituted or substituted by halogen, $C_1$–$C_{12}$alkyl or $C_1$–$C_{12}$alkoxy, with preferably at least one of the substituents X, Y and Z being hydrogen. The substituents X, Y and Z are for example in ortho-, meta- or para-position, preferably in meta- or para-position, to the cyano group.

In particular, the starting materials employed are nitriles of formula (V)

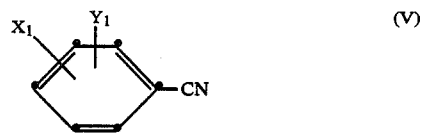
(V)

wherein one of the substituents $X_1$ and $Y_1$ is chlorine, bromine, $C_1$–$C_4$alkyl, cyano, $C_1$–$C_4$alkoxy, phenoxy, which is unsubstituted or substituted by chlorine or methyl, or is carbamoyl, $C_2$–$C_5$alkylcarbamoyl, or phenylcarbamoyl which is unsubstituted or substituted by chlorine, methyl or methoxy, and the other is hydrogen. $X_1$ and $Y_1$ are for example in ortho-, meta- or para-position, preferably in meta- or para-position, to the cyano group.

More particularly, nitriles of formula (V) are employed, wherein one of the substituents $X_1$ and $Y_1$ is chlorine, $C_1$–$C_4$alkyl, preferably ethyl, cyano, or phenyl which is unsubstituted or substituted by chlorine atoms, $C_1$–$C_4$alkyl or $C_1$–$C_4$alkoxy groups, and the other is hydrogen.

Most particularly preferred starting materials are nitriles wherein A and B are radicals of the formula

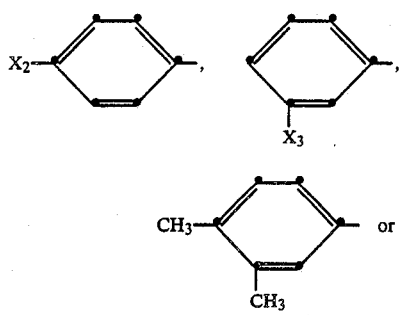

in which formulae $X_2$ is methyl, isobutyl, phenyl, chlorine, bromine, methoxy, phenoxy or cyano, $X_3$ is methyl, chlorine or cyano and $X_4$ is methyl or chlorine or wherein A or B is a β-pyridyl or γ-pyridyl radical, and especially those wherein A is the phenyl, 4-chlorophenyl or 4-biphenylyl radical and B is a phenyl, 3-chlorophenyl, 4-chlorophenyl, 4-methylphenyl, 4-isobutylphenyl, 4-biphenylyl or 3-cyanophenyl radical. Examples of such nitriles are: acetonitrile, propionitrile, butyronitrile, isobutyronitrile, hexyl cyanide, cyclohexyl cyanide, benzyl cyanide, benzonitrile, o-, m- or p-chlorobenzonitrile, o-, m- or p-methylbenzonitrile, p-tert-butylbenzonitrile, p-phenylbenzonitrile, o-, m- or p-methoxybenzonitrile, p-phenoxybenzonitrile, 3,4-dimethylbenzonitrile, isophthalonitrile, terephthalonitrile, 3-pyridyl cyanide or 4-pyridyl cyanide.

It is convenient to use 1.8 to 1.99 moles, preferably 1.9 to 1.98 moles, of the nitrile of the formula ACN and 0.01 to 0.2 mole, preferably 0.02 to 0.1 mole, of the nitrile of the formula BCN or of a mixture of several nitriles different from ACN.

If the nitriles ACN and BCN are aliphatic nitriles, then these may differ by the number of carbon atoms or by the nature and/or position of the substituents. If the nitriles ACN and BCN are carbocyclic or heterocyclic aromatic nitriles, then these may differ by the nature of the ring or by the nature and/or position of any substituents present.

The preferred lactams of formula (II) or enamines of formula (III) are likewise those wherein A is a radical of formula (IV) or (V), and R and R' are $C_1$–$C_6$alkyl groups.

It is preferred to use per mole of the lactam or enamine 0.8 to 0.99 mole, most preferably 0.9 to 0.98 mole, of the nitrile of the formula ACN and 0.01 to 0.2 mole, most preferably 0.02 to 0.1 mole, of the nitrile of the formula BCN or of a mixture containing several nitriles of the formula BCN, the radicals B of which are different from A.

The disuccinates may be dialkyl, diaryl or monoalkyl-monoaryl succinates. The dialkyl and diaryl succinates may also be unsymmetrical. However, it is preferred to use symmetrical disuccinates, most preferably symmetrical dialkyl succinates. If a diaryl or monoaryl-monoalkyl succinate is employed, aryl is preferably phenyl which is unsubstituted or substituted by halogen such as chlorine, $C_1$–$C_6$alkyl such as methyl, ethyl, isopropyl or tert-butyl, or $C_1$–$C_6$alkoxy such as methoxy or ethoxy. The preferred meaning of aryl is unsubstituted phenyl. If a dialkyl or monoalkyl-monoaryl succinate is employed, then alkyl may be unbranched or branched, preferably branched, and may contain preferably 1 to 18, in particular 1 to 12, more particularly 1 to 8 and most preferably 1 to 5, carbon atoms. Branched alkyl is preferably sec-alkyl or tert-alkyl, e.g. isopropyl, sec-butyl, tert-butyl or tert-amyl.

Examples of disuccinates are: dimethyl succinate, diethyl succinate, dipropyl succinate, dibutyl succinate, dipentyl succinate, dihexyl succinate, diheptyl succinate, dioctyl succinate, diisopropyl succinate, di-sec-butyl succinate, di-tert-butyl succinate, di-tert-amyl succinate, di-[1,1-dimethylbutyl]succinate, di-[1,1,3,3-tetramethylbutyl]succinate, di-[1,1-dimethylpentyl]succinate, di-[1-methyl-1-ethylbutyl]succinate, di-[1,1-diethylpropyl]succinate, diphenyl succinate, di-[4-methylpentyl]succinate, di-[2-methylphenyl]succinate, di-[4-chlorophenyl]succinate and monoethyl-monophenyl succinate.

The disuccinates and the nitriles of the formulae ACN and BCN are known compounds and can be prepared by known methods.

The reaction of the disuccinate or of the lactam of formula (II) or the enamine of formula (III) with the nitriles is carried out in an organic solvent. Examples of suitable solvents are: primary, secondary or tertiary alcohols containing 1 to 10 carbon atoms, e.g. methanol, ethanol, n-propanol, isopropanol, n-butanol, sec-butanol, tert-butanol, n-pentanol, 2-methyl-2-butanol, 2-methyl-2-pentanol, 3-methyl-3-pentanol, 2-methyl-2-hexanol, 3-ethyl-3-pentanol, 2,4,4-trifluoromethyl-2-pentanol, or glycols such as ethylene glycol or diethylene glycol; and also ethers such as tetrahydrofuran or dioxane, or glycol ethers such as ethylene glycol methyl ether, ethylene glycol ethyl ether, diethylene glycol monomethyl ether or diethylene glycol monoethyl ether; as well as dipolar aprotic solvents such as acetonitrile, benzonitrile, dimethylformamide, N,N-dimethylacetamide, nitrobenzene or N-methylpyrrolidone; aliphatic or aromatic hydrocarbons such as benzene or benzene substituted by alkyl, alkoxy or halogen, e.g. toluene, xylene, anisole or chlorobenzene; or aromatic N-heterocyclic compounds such as pyridine, picoline or quinoline. It is also possible to use the nitrile of the formula ACN or BCN simultaneously as a solvent if it is in the liquid state in the temperature range in which the reaction is carried out. The above solvents may also be used in mixtures. It is convenient to employ 5 to 20 parts by weight of solvent per 1 part by weight of the reactants. It is preferred to use an alcohol as solvent, most preferably a secondary or tertiary alcohol. Preferred tertiary alcohols are tert-butanol and tert-amyl alcohol.

The reaction is carried out in the presence of a strong base. Examples of suitable bases are: alkali metal hydroxides such as sodium, potassium or lithium hydroxide, or alkaline earth metal hydroxides such as calcium or magnesium hydroxide, or alkali metal amides such as lithium amide or sodium amide, or alkali metal hydrides such as lithium hydride or sodium hydride, or alkaline earth metal alcoholates or alkali metal alcoholates which are derived preferably from primary, secondary or tertiary aliphatic alcohols containing 1 to 10 carbon atoms, e.g. sodium, potassium or lithium methylate, sodium, potassium or lithium ethylate, sodium, potassium or lithium n-propylate, sodium, potassium or lithium isopropylate, sodium, potassium or lithium n-butylate, sodium, potassium or lithium sec-butylate, sodium, potassium or lithium tert-butylate, sodium, potassium or lithium 2-methyl-2-butylate, sodium, potassium or lithium 2-methyl-2-pentylate, sodium, potassium or lithium 3-methyl-3-pentylate, sodium, potassium or lithium 3- ethyl-3-pentylate, or alkaline earth metal phenolates, alkaline earth metal o-alkyl substituted phenolates, alkali metal phenolates or alkali metal o-alkyl substituted phenolates, e.g. sodium or potassium o-cresolate. However, a mixture of the above bases may also be employed.

Preferred strong bases are alkali metal alcoholates, the alkali metal preferably being sodium or potassium and the alcoholate being preferably derived from a secondary or tertiary alcohol. Particularly preferred strong bases are therefore e.g. sodium or potassium isopropylate, sodium or potassium sec-butylate, sodium or potassium tert-butylate and sodium or potassium tert-amylate.

The strong base may be employed in an amount of preferably 0.1 to 4 moles, most preferably 1.9 to 2.2 moles, based on the disuccinate or lactam reactant. Depending on the reactants and the procedure, e.g. recyclisation, smaller amounts of base may have quite an advantageous effect on the yield. On the other hand, in certain cases an excess of base may have an advantageous influence on the yield. Usually, however, stoichiometric amounts of base suffice.

The above strong bases may be employed together with a phase transfer catalyst. This is especially advantageous if the solubility of a particular base in a particular solvent is low. The phase transfer catalysts may be employed in an amount of 0.001 to 50 mol%, preferably 0.01 to 0.3 mol%, based on the disuccinate reactant. Suitable phase transfer catalysts for the process of this invention are the conventional phase transfer catalysts described in the literature, e.g. those listed in CHEMTECH, February 1980, p. 111, Table 1, namely e.g. quaternary salts, cyclic polyethers, open chain polyethers, N-alkylphosphoramides or phosphorus or sulfur oxides containing a methylene bridge.

The reaction is preferably carried out at a temperature in the range from 60° to 140° C., most preferably from 80° to 120° C.

In order to react the disuccinate with the nitriles, it is in principle possible to charge the reaction vessel, at a lower temperature, with all the components and then to heat the reaction mixture to the range of the reaction temperature, or to add the individual components, in any order, to one another in the range of the reaction temperature.

A preferred embodiment, which usually has an advantageous influence on the yield, comprises charging the reaction vessel with the nitrile of the formula ACN together with the nitrile of the formula BCN or together with a mixture of several nitriles different from ACN, in the presence of the base, and then adding the disuccinate or the lactam of formula (II) or the enamine of formula (III) in the range of the reaction temperature.

In particular in the case of disuccinates containing lower alkyl moieties and of alcoholates which are derived from lower alcohols such as methanol, ethanol, n-propanol, isopropanol or tert-butanol, in order to obtain higher yields, it may prove necessary to remove continuously from the reaction medium the lower alcohol forming during the reaction.

If the solvent employed is an alcohol and the base an alcoholate, it may be advantageous to select an alcohol and an alcoholate containing the same alkyl moieties. It may also be of advantage if the disuccinate also contains such alkyl groups.

The hydrolysis of the condensation product may be carried out with an acid, an alcohol containing 1 to 4 carbon atoms, e.g. methanol or ethanol, but preferably with water. Examples of suitable acids are: aliphatic or aromatic carboxylic or sulfonic acids, e.g. formic acid, acetic acid, propionic acid, oxalic acid, benzoic acid or benzenesulfonic acid. Further suitable acids are also mineral acids, e.g. hydrochloric acid, aqueous solutions thereof, as well as carbonic acid, dilute sulfuric acid and dilute phosphoric acid.

The mixture of pigments precipitates during hydrolysis and may be isolated by filtration.

In order to achieve an additional improvement of the pigment forms, the mixtures of pigments obtained in accordance with the process of this invention may, after hydrolysis in the reaction mixture or after isolation of the pigment, be subjected to aftertreatment in water or in an organic solvent, with or without pressure. It is preferred to employ an organic solvent having a boiling point above 80° C. Particularly suitable solvents are benzenes which are substituted by halogen atoms or by alkyl or nitro groups, e.g. xylenes, chlorobenzene, o-dichlorobenzene or nitrobenzene, as well as pyridine bases such as pyridine, picoline or quinoline, and also ketones such as cyclohexanone, ethers such as ethylene glycol monomethyl or monoethyl ether, amides such as dimethylformamide or N-methylpyrrolidone, and also dimethyl sulfoxide or sulfolane. The aftertreatment may also be carried out in water in the presence of an organic solvent and/or with the addition of surface-active compounds.

Particularly transparent pigment forms are obtained if the resultant mixtures of pigments are subjected to subsequent comminution such as wet grinding.

The resultant mixture of pigments is novel and can be used for pigmenting organic material of high molecular weight, e.g. cellulose ethers and esters such as ethyl cellulose, nitrocellulose, cellulose acetate, cellulose butyrate, natural resins or synthetic resins such as polymerisation resins or condensation resins, aminoplasts, in particular urea/formaldehyde and melamine/formaldehyde resins, alkyd resins, phenolic plastics, polycarbonates, polyolefins, polystyrene, polyvinyl chloride, polyamides, polyurethanes, polyesters, rubber, casein, silicone and silicone resins, individually or in mixtures.

The above organic compounds of high molecular weight, individually or in mixtures, may be in the form of plastics, melts or of spinning solutions, lacquers, paints or printing inks. Depending on the end use, it is advantageous to use the pigments of this invention in the form of toners or formulations. The mixture of pigments is employed in an amount of preferably 0.1 to 10% by weight, based on the organic material of high molecular weight to be pigmented.

Compared with the homogeneous pigments known from U.S. Pat. No. 4,415,685, the mixtures of pigments obtained in accordance with the process of this invention have the following different advantages:
with respect to the form and size of the particles, they can be better controlled during synthesis and/or conditioning
they have greater colour strength and are more transparent
they exhibit a lower tendency to recrystallise during synthesis and/or conditioning
they have higher storage stability in solvents, in particular in solvents containing lacquers and printing inks they have better heat stability in plastics, which results in a consistency of shade and colour strength at various processing temperatures on account of their greater transparency and colour strength, they are more suitable for the mass colouration of filaments in some cases they may produce unexpected shades having interesting properties.

The colourations obtained with the mixtures of pigments of the present invention, e.g. in plastics, filaments, lacquers or printing inks, also have good dispersibility, good fastness to overspraying, migration, heat, light and atmospheric influences, as well as good gloss.

The invention is illustrated by the following examples.

EXAMPLE 1

27.6 g of sodium and 0.4 g of the sodium salt of bis-2-ethylhexyl sulfosuccinate are stirred at reflux temperature in 480 ml of tert-amyl alcohol until all is dissolved. The reaction mixture is cooled to 90° C. and 104.6 g of 4-chlorobenzonitrile and 4.1 g of benzonitrile are added, followed by the addition over 3 hours of 81.2 g of diisopropyl succinate. The reaction mixture is allowed to react for 1 hour at reflux temperature and is then poured into 800 ml of water. The hydrolysis mixture is boiled for 1 hour and steam is subsequently introduced for 1 hour in order to remove the organic solvent. The pigment suspension is filtered and the filter cake is washed with water and methanol and dried in vacuo at 80° C., affording 106.3 g of pigment which colours PVC red.

| C, H, N analysis: | C | H | N |
|---|---|---|---|
| found: | 61.04 | 3.01 | 7.79 |

EXAMPLE 2

6.9 g of sodium and 0.1 g of the sodium salt of bis-2-ethylhexyl sulfosuccinate are stirred at reflux temperature in 120 ml of tert-amyl alcohol until all is dissolved. The reaction mixture is cooled to 90° C. and 21.6 g of 4-chlorobenzonitrile and 1.6 g of 4-tert-butylbenzonitrile are added, followed by the addition over 3 hours of 20.3 g of diisopropyl succinate. The reaction mixture is boiled for 1 hour at reflux temperature and then poured into 200 ml of water. The hydrolysed product is worked up in accordance with the procedure described in Example 1, affording 26.3 g of pigment which colours PVC red.

| C, H, N analysis: | C | H | N |
|---|---|---|---|
| found: | 61.00 | 3.19 | 7.71 |

EXAMPLE 3

The procedure of Example 2 is repeated, using a nitrile mixture consisting of 26.1 g of 3-chlorobenzonitrile and 1.3 g of isophthalonitrile. The resultant mixture of pigments (26.3 g) colours PVC orange.

EXAMPLE 4

The procedure of Example 2 is repeated, using a nitrile mixture consisting of 30.2 g of 4-tert-butylbenzonitrile and 1.4 g of 3-chlorobenzonitrile and carrying out condensation at 105° C. 21.1 g of pigment which colours PVC reddish orange are isolated.

EXAMPLE 5

A 1.5 liter glass container is charged with 500 ml of tert-amyl alcohol and nitrogen is then slowly introduced. 27.6 g of sodium followed by 0.4 g of the sodium salt of bis-2-ethylhexyl sulfosuccinate as emulsifier are added to the tert-amyl alcohol and the reaction mixture is slowly heated to 95°–102° C. With efficient stirring, the melted metal is dissolved in the alcohol. The resultant solution is cooled to about 80° C. and 81.6 g of benzonitrile and 1.1 g of p-chlorobenzonitrile are added. The mixture is heated to 110° C. and, with the introduction of nitrogen and with stirring, 80.8 g of diisopropyl succinate are slowly added dropwise over 3 hours, while simultaneously distilling off the isopropanol forming. Towards the end of the reaction the temperature drops to 104° C. The resultant pigment suspension is allowed to react for 2 hours, while simultaneously distilling off a small amount of isopropanol and tert-amyl alcohol. A beaker is charged with 700 ml of water (15°–25° C.) and, with good stirring, the pigment suspension is introduced over about 3 minutes. The resultant two-phase mixture is stirred for 1 hour, poured into a glass vessel equipped with a cooler, then heated to reflux temperature and stirred under reflux for 6 hours. The solvent is then distilled off by the introduction of steam. The resultant aqueous pigment suspension is filtered hot and the filter cake is washed with hot water, dried in a vacuum shelf dryer at 80° C. and then pulverised, affording 70 g of a red pigment powder which colours PVC red.

EXAMPLE 6

The procedure of Example 5 is repeated, using 80.0 g, instead of 81.6 g, of benzonitrile and 3.4 g, instead of 1.1 g, of p-chlorobenzonitrile. A mixture of pigments with properties equally as good as those of the mixture of Example 5 is obtained.

EXAMPLES 7 TO 16

The procedure of Example 2 is repeated, using the nitriles listed in the following Table as ACN and BCN.

| Example | ACN | BCN |
|---|---|---|
| 7 | 26.7 g 4-chlorobenzonitrile | 0.8 g isophthalonitrile |
| 8 | 26.1 g 4-chlorobenzonitrile | 1.3 g isophthalonitrile |
| 9 | 24.8 g 4-chlorobenzonitrile | 2.6 g isophthalonitrile |
| 10 | 27.2 g 4-chlorobenzonitrile | 0.4 g 4-cyanobiphenyl |
| 11 | 26.7 g 4-chlorobenzonitrile | 1.1 g 4-cyanobiphenyl |
| 12 | 26.1 g 4-chlorobenzonitrile | 1.8 g 4-cyanobiphenyl |
| 13 | 24.8 g 4-chlorobenzonitrile | 3.6 g 4-cyanobipheyl |
| 14 | 26.7 g 4-chlorobenzonitrile | 0.6 g 4-cyanopyridine |
| 15 | 26.1 g 4-chlorobenzonitrile | 1.1 g 4-cyanopyridine |
| 16 | 24.8 g 4-chlorobenzonitrile | 2.1 g 4-cyanopyridine |

EXAMPLES 17 TO 23

The procedure of Example 2 is repeated, using the nitriles listed in the following Table as ACN and BCN.

| Example | ACN | BCN |
|---|---|---|
| 17 | 34.3 g 4-cyanobiphenyl | 1.0 g benzonitrile |
| 18 | 32.5 g 4-cyanobiphenyl | 2.1 g benzonitrile |
| 19 | 34.3 g 4-cyanobiphenyl | 1.3 g isophthalonitrile |

-continued

| Example | ACN | BCN |
|---|---|---|
| 20 | 34.3 g 4-cyanobiphenyl | 1.4 g 4-chlorobenzonitrile |
| 21 | 32.5 g 4-cyanobiphenyl | 2.8 g 4-chlorobenzonitrile |
| 22 | 34.3 g 4-cyanobiphenyl | 1.6 g 4-t-butylbenzonitrile |
| 23 | 32.5 g 4-cyanobiphenyl | 3.2 g 4-t-butylbenzonitrile |

EXAMPLE 24

0.7 g of sodium and 10 mg of the sodium salt of bis-2-ethylhexyl sulfosuccinate (emulsifier) in 30 ml of tert-amyl alcohol are stirred at reflux temperature until all is dissolved. Over 10 minutes, 1.7 g of 3-ethoxycarbonyl-2-methyl-2-pyrrolin-5-one, 0.90 g of benzonitrile and 0.14 g of p-chlorobenzonitrile are added and the reaction mixture is stirred for 17 hours at 90° C. The yellow suspension is cooled to 60° C., poured into 30 ml of ice water, adjusted to pH 7 with 1N HCl and filtered with suction and the filter cake is washed with water and dried. The crude product is stirred for 3 hours in methanol at reflux temperature, the methanolic solution is filtered and the filter cake is dried in a vacuum furnace at 70° C. The resultant mixture of pigments (1.3 g) colours PVC orange.

| C, H, N, Cl analysis: | C | H | N | Cl |
|---|---|---|---|---|
| found: | 67.80 | 4.37 | 12.06 | 1.2 |

EXAMPLE 25

3.6 g of potassium tert-butoxide are added in portions to a suspension of 2.1 g of 4-chlorobenzonitrile, 0.30 g of 4-phenylbenzonitrile and 3.3 g of 2-ethoxycarbonyl-2-phenyl-2-pyrrolin-5-one in 30 ml of tert-butanol and stirred for 5 hours at reflux temperature. The suspension is cooled to 60° C. and diluted with 50 ml of methanol and 3 ml of acetic acid are added. After cooling, the solid is isolated by suction filtration, washed with methanol, dried and stirred for 3 hours in methanol at reflux temperature. The methanolic solution is cooled and filtered with suction and the filter cake is dried in a vacuum furnace at 70° C. The resultant mixture of pigments (1.6 g) colours PVC red.

| C, H, N analysis: | C | H | N | Cl |
|---|---|---|---|---|
| found: | 66.84 | 3.60 | 8.47 | 10.2 |

EXAMPLE 26

The procedure of Example 25 is repeated, using 1.7 g of 4-chlorobenzonitrile, 2.2 g of 4-phenylbenzonitrile, 4.3 g of 3-ethoxycarbonyl-2-phenyl-2-pyrrolin-5-one and 4.8 g of potassium tert-butoxide. 3.1 g of a mixture of pigments which colours PVC red are isolated.

| C, H, N, Cl analysis: | C | H | N | Cl |
|---|---|---|---|---|
| found: | 70.60 | 3.85 | 8.23 | 7.26 |

EXAMPLE 27

The procedure of Example 25 is repeated, using 0.16 g of 4-chlorobenzonitrile, 4.1 g of 4-phenylbenzonitrile, 4.3 g of 3-ethoxycarbonyl-2-phenyl-2-pyrrolin-5-one and 4.8 g of potassium tert-butoxide. 2.9 g of a mixture of pigments which colours PVC red are isolated.

| C, H, N, Cl analysis: | C | H | N | Cl |
|---|---|---|---|---|
| found: | 78.00 | 4.54 | 7.65 | 0.72 |

EXAMPLE 28

The procedure of Example 25 is repeated, using 2.4 g of benzonitrile, 0.16 g of 4-chlorobenzonitrile, 4.3 g of 3-ethoxycarbonyl-2-phenyl-2-pyrrolin-5-one and 4.3 g of potassium tert-butoxide. 2.1 g of a mixture of pigments which colours PVC red are isolated.

| C, H, N, Cl analysis: | C | H | N | Cl |
|---|---|---|---|---|
| found: | 73.59 | 4.24 | 9.59 | 1.1 |

EXAMPLE 29

A mixture of 130 g of steatite beads of 8 mm diameter, 47.5 g of alkyd melamine stoving varnish consisting of 60 g of a 60% solution of Beckosol 27-320 ® (Reichhold Chemie AG) in xylene and of 36 g of a 50% solution of Super Beckamin 13-501 ® (Reichhold Chemie AG) in a mixture of 2 g of xylene and 2 g of ethylene glycol monomethyl ether, and 2.5 g of the mixture of pigments obtained according to Example 5 or 6 is dispersed in a glass flask with a twist off cap for 120 hours on a roller gear bed. After removal of the steatite beads, the varnish is applied to white board and subsequently stoved for 30 minutes at 130° C. (Thickness of the varnish layer=about 50 μm).

The shade of the varnish coloured in this manner is characterised as follows in accordance with DIN 6174:

| | L* | A* | B* |
|---|---|---|---|
| Mixture of pigments according to Example 5 | 45.20 | 51.23 | 29.86 |
| Mixture of pigments according to Example 6 | 44.30 | 50.13 | 27.97 |

EXAMPLE 30

0.6 g of the mixture of pigments obtained according to Example 1 is mixed with 67 g of polyvinyl chloride, 33 g of dioctyl phthalate, 2 g of dibutyltin dilaurate and 2 g of titanium dioxide and the mixture is processed to a thin sheet for 15 minutes at 160° C. on a roll mill. The red colouration so obtained is strong and is resistant to migration and light.

EXAMPLE 31

A mixture of 1.0 g of the mixture of pigments obtained according to Example 5, 1.0 g of the antioxidant IRGANOX 1010 ® (registered trade mark of CIBA-GEIGY AG) and 1000.0 g of polyethylene HD granulate VESTOLEN A-60-16 ® (registered trade mark of HUELS) is premixed for 15 minutes in a 3 liter glass flask on a Röhnrad mixer. The mixture is subsequently extruded in a single screw extruder and the resultant granulate is processed to boards at 220° C. in an Allround Aarburg 200 ® injection moulding machine and the boards are after-pressed for 5 minutes at 180° C. The boards are coloured in strong red shades of excellent fastness properties.

EXAMPLE 32

The procedure of Example 31 is repeated, processing the coloured granulate at 270° C. instead of 220° C. Similarly coloured boards are obtained.

EXAMPLE 33

1000 g of polypropylene granulate DAPLEN PT-55 ® (registered trade mark of CHEMIE LINZ) and 20 g of a 50% pigment formulation consisting of 10 g of the mixture of pigments obtained according to Example 5 and 10 g of magnesium behenate are mixed thoroughly in a mixing drum. The treated granulate is melt spun at 260° to 285° C. Red coloured fibres of good lightfastness and textile properties are obtained.

What is claimed is:

1. A mixture of pigments containing at least two different pigments of formula (I)

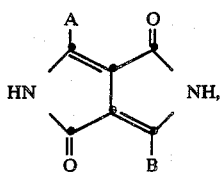

(I)

with the difference lying in the meanings of the radicals A and B, in which formula (I) A and B are the same or different alkyl, aralkyl, cycloalkyl, carbocyclic or heterocyclic aromatic radicals, which mixture of pigments is obtainable by (a) reacting in a molar ratio 1 mole of a disuccinate with 1.75 to 1.998 moles of a nitrile of the formula ACN and 0.002 to 0.25 mole of a nitrile of the formula BCN or of a mixture of several nitriles of the formula BCN, the radicals B of which are different from A, or (b) reacting in a molar ratio 1 mole of a lactam of formula (II) or of an enamine of formula (III)

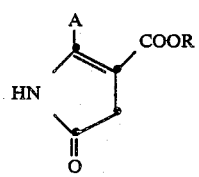

(II)

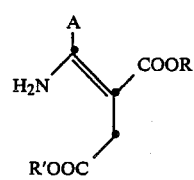

(III)

in which formulae each of R and R' independently of the other is alkyl or aryl, with 0.75 to 0.998 mole of a nitrile of the formula ACN and 0.25 to 0.002 mole of a nitrile of the formula BCN or of a mixture of several nitriles of the formula BCN, the radicals B of which are different from A, in an organic solvent, in the presence of a strong base and at elevated temperature, and subsequently hydrolysing the resultant reaction product.

2. A mixture of pigments according to claim 1, obtainable by using per mole of a disuccinate or of the lactam of formula (II) or of the enamine of formula (III) 1.8 to 1.99 or 0.8 to 0.99 moles of the nitrile of the formula ACN and 0.01 to 0.2 mole of the nitrile of the formula BCN or of a mixture of several nitriles of the formula BCN, the radicals B of which are different from A.

3. A mixture of pigments according to claim 1, obtainable by using per mole of a disuccinate or of the lactam of formula (II) or of the enamine of formula (III) 1.9 to 1.98 or 0.9 to 0.98 moles of the nitrile of the formula ACN and 0.02 to 0.1 mole of the nitrile of the formula BCN or of a mixture of several nitriles of the formula BCN, the radicals B of which are different from A.

4. A mixture of pigments according to claim 1, obtainable by using a homogeneous nitrile BCN.

5. A mixture of pigments according to claim 1, obtainable by starting from nitriles of the formulae ACN and BCN, wherein A and B are carbocyclic or heterocyclic aromatic radicals.

6. A mixture of pigments according to claim 1, obtainable by starting from nitriles of the formulae ACN and BCN, wherein A and B are radicals of the formula

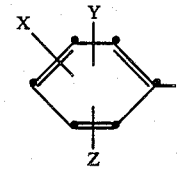

which differ with respect to their chemical properties and/or the position of the substituents X, Y and Z, in which formula each of X, Y and Z independently is hydrogen, halogen, carbamoyl, cyano, trifluoromethyl, $C_2$-$C_{13}$alkylcarbamoyl, $C_1$-$C_{12}$alkyl, $C_1$-$C_{12}$alkoxy, $C_1$-$C_{12}$alkylmercapto, $C_2$-$C_{13}$alkoxycarbonyl, $C_2$-$C_{13}$alkanoylamino, $C_1$-$C_{12}$monoalkylamino, $C_2$-$C_{24}$dialkylamino, or is phenoxy, phenylmercapto, phenoxycarbonyl, phenylcarbamoyl or benzoylamino, each unsubstituted or substituted by halogen, $C_1$-$C_{12}$alkyl or $C_1$-$C_{12}$alkoxy.

7. A mixture of pigments according to claim 6, wherein at least one of the substituents X, Y and Z is hydrogen.

8. A mixture of pigments according to claim 1, obtainable by starting from nitriles of the formulae ACN and BCN, wherein A and B are radicals of the formula

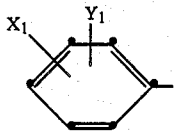

which differ with respect to their chemical properties and/or the position of the substituents $X_1$ and $Y_1$, in which formula each of the substituents $X_1$ and $Y_1$ independently of the other is chlorine, bromine, $C_1$-$C_4$alkyl, cyano, $C_1$-$C_4$alkoxy, phenoxy which is unsubstituted or substituted by chlorine or methyl, or is carbamoyl, $C_2$-$C_5$alkylcarbamoyl, or phenylcarbamoyl which is unsubstituted or substituted by chlorine, methyl or methoxy.

9. A mixture of pigments according to claim 8, wherein one of the substituents $X_1$ and $Y_1$ is hydrogen.

10. A mixture of pigments according to claim 1, obtainable by starting from nitriles of the formulae ACN and BCN, wherein A and B are radicals of the formula

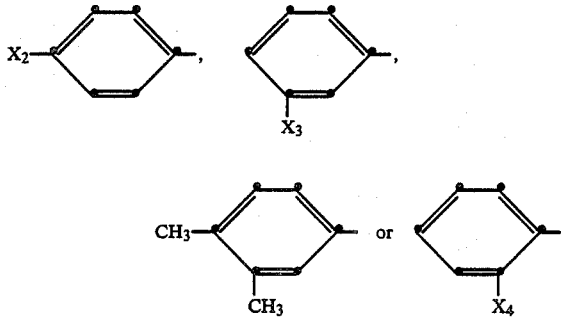

in which formulae $X_2$ is methyl, isobutyl, chlorine, bromine, methoxy, phenoxy or cyano, $X_3$ is methyl, chlorine or cyano and $X_4$ is methyl or chlorine, or wherein A or B is a $\beta$-pyridyl or $\gamma$-pyridyl radical.

11. A mixture of pigments according to claim 1, obtainable by starting from nitriles, wherein A is the phenyl, 4-chlorophenyl or 4-biphenylyl radical and B is the phenyl, 3-chlorophenyl, 4-chlorophenyl, 4-methylphenyl, 4-isobutylphenyl, 4-bisphenylyl or 3-cyanophenyl radical.

12. A mixture of pigments according to claim 1, obtainable by using benzonitrile as the nitrile of the formula ACN and p-chlorobenzonitrile as the nitrile of the formula BCN.

13. A mixture of pigments according to claim 1, obtainable by using p-chlorobenzonitrile as the nitrile of the formula ACN and isophthalonitrile as the nitrile of the formula BCN.

14. A mixture of pigments according to claim 1, obtainable by using p-chlorobenzonitrile as the nitrile of the formula ACN and 4-cyanobiphenyl as the nitrile of the formula BCN.

15. A mixture of pigments according to claim 1, obtainable by using p-chlorobenzonitrile as the nitrile of the formula ACN and 4-cyanopyridine as the nitrile of the formula BCN.

* * * * *